US008927773B2

(12) United States Patent
Klasovsky et al.

(10) Patent No.: US 8,927,773 B2
(45) Date of Patent: Jan. 6, 2015

(54) PROCESS FOR THE DIRECT AMINATION OF SECONDARY ALCOHOLS WITH AMMONIA TO GIVE PRIMARY AMINES

(75) Inventors: Florian Klasovsky, Haltern am See (DE); Jan Christoph Pfeffer, Hanau (DE); Thomas Tacke, Alzenau (DE); Thomas Haas, Muenster (DE); Andreas Martin, Berlin (DE); Jens Deutsch, Rangsdorf (DE); Angela Koeckritz, Berlin (DE)

(73) Assignee: Evonik Degussa GmbH, Essen (DE)

( * ) Notice: Subject to any disclaimer, the term of this patent is extended or adjusted under 35 U.S.C. 154(b) by 10 days.

(21) Appl. No.: 13/820,803

(22) PCT Filed: Aug. 23, 2011

(86) PCT No.: PCT/EP2011/064435
§ 371 (c)(1),
(2), (4) Date: Mar. 5, 2013

(87) PCT Pub. No.: WO2012/031884
PCT Pub. Date: Mar. 15, 2012

(65) Prior Publication Data
US 2013/0165672 A1    Jun. 27, 2013

(30) Foreign Application Priority Data

Sep. 10, 2010 (DE) .......................... 10 2010 040 560
Feb. 21, 2011 (DE) .......................... 10 2011 004 465

(51) Int. Cl.
| C07C 209/00 | (2006.01) |
| C07C 209/16 | (2006.01) |
| C07C 213/02 | (2006.01) |
| C07D 493/04 | (2006.01) |

(52) U.S. Cl.
CPC ............. *C07C 209/16* (2013.01); *C07C 213/02* (2013.01); *C07D 493/04* (2013.01)
USPC ........... 564/480; 564/447; 564/474; 564/487; 549/464

(58) Field of Classification Search
None
See application file for complete search history.

(56) References Cited

U.S. PATENT DOCUMENTS

| 4,855,425 | A | 8/1989 | Marsella |
| 5,530,127 | A | 6/1996 | Reif et al. |
| 7,148,176 | B2 | 12/2006 | Beller et al. |
| 7,758,897 | B2 | 7/2010 | Roettger et al. |
| 8,372,595 | B2 | 2/2013 | Schaffer et al. |
| 8,378,127 | B2 | 2/2013 | Dingerdissen et al. |
| 8,604,227 | B2 | 12/2013 | Petrat et al. |
| 2001/0047097 | A1 | 11/2001 | Trauthwein et al. |
| 2002/0087036 | A1 | 7/2002 | Haas et al. |
| 2003/0212298 | A1 | 11/2003 | Brasse et al. |
| 2007/0207501 | A1 | 9/2007 | Wolf et al. |
| 2010/0068773 | A1 | 3/2010 | Marx et al. |
| 2010/0190224 | A1 | 7/2010 | Poetter et al. |
| 2010/0261237 | A1 | 10/2010 | Verseck et al. |
| 2010/0291644 | A1 | 11/2010 | Marx et al. |
| 2010/0324257 | A1 | 12/2010 | Karau et al. |
| 2011/0039313 | A1 | 2/2011 | Verseck et al. |
| 2011/0039977 | A1 | 2/2011 | Schuetz et al. |
| 2011/0118433 | A1 | 5/2011 | Pötter et al. |
| 2011/0118504 | A1 | 5/2011 | Haas et al. |
| 2011/0152525 | A1 | 6/2011 | Milstein et al. |
| 2011/0171702 | A1 | 7/2011 | Reinecke et al. |
| 2011/0189742 | A1 | 8/2011 | Haas et al. |
| 2011/0251399 | A1 | 10/2011 | Dingerdissen et al. |
| 2011/0257429 | A1 | 10/2011 | Schraven et al. |
| 2012/0034665 | A1 | 2/2012 | Haas et al. |
| 2012/0041216 | A1 | 2/2012 | Sieber et al. |
| 2012/0245375 | A1 | 9/2012 | Hannen et al. |
| 2012/0264182 | A1 | 10/2012 | Reinecke et al. |
| 2013/0052700 | A1 | 2/2013 | Poetter et al. |
| 2013/0092233 | A1 | 4/2013 | Pawlik et al. |
| 2013/0130319 | A1 | 5/2013 | Schaffer et al. |
| 2013/0165685 | A1 | 6/2013 | Hannen et al. |
| 2013/0183725 | A1 | 7/2013 | Poetter et al. |

FOREIGN PATENT DOCUMENTS

| EP | 0 696 572 | 2/1996 |
| GB | 2 059 792 | 4/1981 |
| WO | 2010 018570 | 2/2010 |
| WO | 2012 076560 | 6/2012 |
| WO | 2012 113475 | 8/2012 |

OTHER PUBLICATIONS

Imm et al, Angew.Chem.Int.Ed., 2010, 49, 8126-8129.*
U.S. Appl. No. 13/989,419, filed May 24, 2013, Klasovsky, et al.
U.S. Appl. No. 14/000,067, filed Aug. 16, 2013, Erhardt, et al.
U.S. Appl. No. 14/000,028, filed Aug. 16, 2013, Erhardt, et al.

(Continued)

*Primary Examiner* — Sudhakar Katakam
(74) *Attorney, Agent, or Firm* — Oblon, Spivak, McClelland, Maier & Neustadt, L.L.P.

(57) ABSTRACT

The invention relates to a process for preparing primary amines which comprises the process steps A) provision of a solution of a secondary alcohol in a fluid, nongaseous phase, B) contacting of the phase with free ammonia and/or at least one ammonia-releasing compound and a homogeneous catalyst and optionally C) isolation of the primary amine formed in process step B), characterized in that the volume ratio of the volume of the liquid phase to the volume of the gas phase in process step B is greater than or equal to 0.25, and/or in that the ammonia is used in process step B) in a molar ratio based on the hydroxyl groups in the secondary alcohol of at least 5:1.

13 Claims, 1 Drawing Sheet

(56) References Cited

OTHER PUBLICATIONS

Gunanathan, C., et al., "Selective Synthesis of Primary Amines Directly from Alcohols and Ammonia," Angewandte Chemie, vol. 47, No. 45, pp. 8661-8664, (Jan. 1, 2008) XP 2554983.
Imm, S., et al., "Improved Ruthenium-Catalyzed Amination of Alcohols with Ammonia: Synthesis of Diamines and Amino Esters," Angewandte Chemie, vol. 50, pp. 7599-7603, (Jul. 5, 2011) XP 2664616.
International Search Report Issued Dec. 7, 2011 in PCT/EP11/64435 Filed Aug. 23, 2011.
U.S. Appl. No. 14/237,121, filed Feb. 4, 2014, Haas, et al.
U.S. Appl. No. 14/233,505, filed Jan. 17, 2014, Poetter, et al.
U.S. Appl. No. 14/238,576, filed Feb. 12, 2014, Schaffer, et al.
U.S. Appl. No. 14/238,591, filed Feb. 12, 2014, Schaffer, et al.
U.S. Appl. No. 09/424,701, filed Jan. 25, 2002, Beller, et al.
U.S. Appl. No. 14/110,450, filed Oct. 8, 2013, Klasovsky, et al.
U.S. Appl. No. 14/126,607, filed Dec. 16, 2013, Haas, et al.
U.S. Appl. No. 14/363,178, filed Jun. 5, 2014, Haas, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/380,483, filed Aug. 22, 2014, Schiemann, et al.

\* cited by examiner

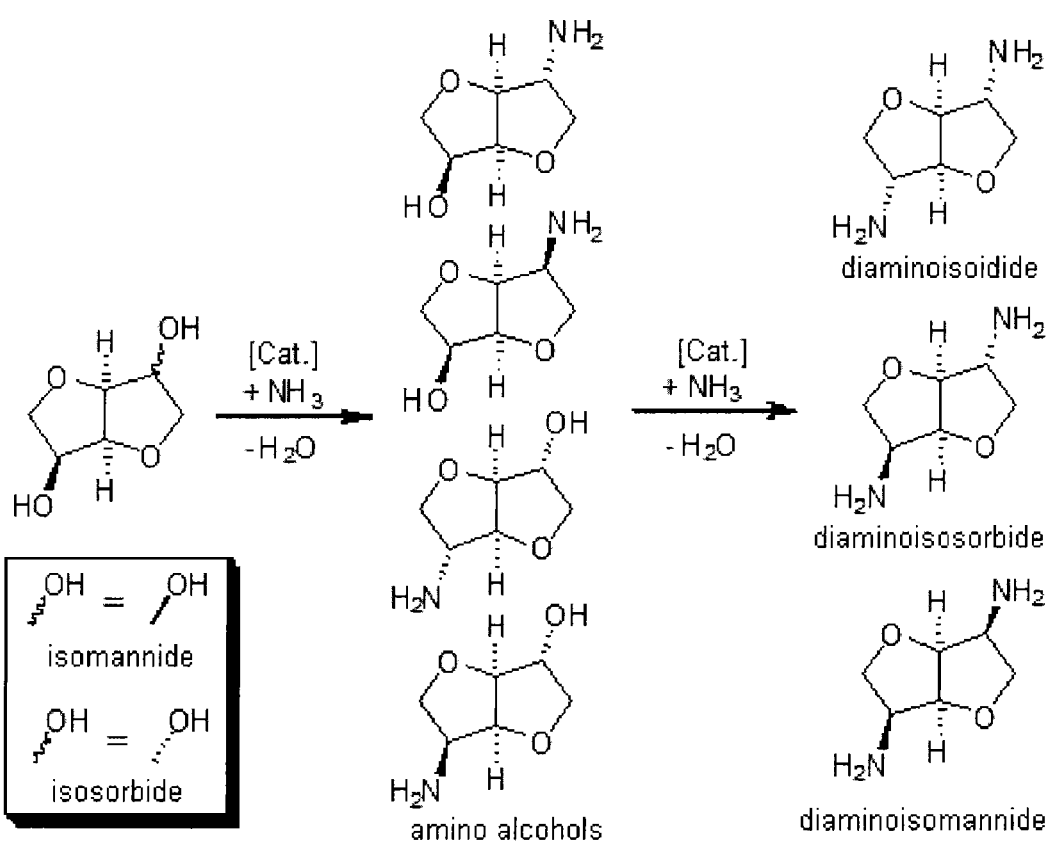

PROCESS FOR THE DIRECT AMINATION OF SECONDARY ALCOHOLS WITH AMMONIA TO GIVE PRIMARY AMINES

The present invention relates to a chemocatalytic liquid-phase process for the direct single-stage amination of optionally polyhydric and/or functionalized secondary alcohols to optionally polyvalent and/or functionalized primary amines by means of ammonia in high yields with the aid of a homogeneous catalyst system.

PRIOR ART

The conversion of oxygen-containing functional groups into nitrogen-containing functional groups represents an essential transformation for the synthesis of many organic compounds. A series of classical methods are known in the literature and industry in order to achieve the stated object. In the great majority of publications, a primary or secondary alcohol is reacted with a primary or secondary organic amine. The reaction of a primary or secondary alcohol with ammonia to form primary amines as per scheme 1, on the other hand, has been described only for use of particular process conditions, catalysts and only for a few alcohols.

Scheme 1: General reaction scheme for obtaining primary amines from primary or secondary alcohols

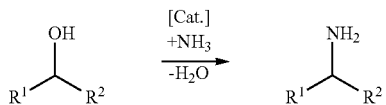

The challenge faced by all known processes is to achieve high selectivities to the primary amines, since these are more nucleophilic than ammonia and consequently can react preferentially to form higher amines. While the conversion of an isolated hydroxyl function into an amino function is approximately thermally neutral, the formation of secondary and tertiary amines is exothermic with an enthalpy of reaction of in each case about 30 kJ/mol and is therefore also thermodynamically preferred over the formation of primary amines.

DIRECT AMINATION IN THE GAS PHASE

The single-stage direct conversion of a primary or secondary hydroxyl group by means of ammonia into a primary amine is in the case of lower, readily vaporizable alcohols restricted mainly to gas-phase reactions. Here, the appropriate alcohol is vaporized and reacted under suitable conditions (pressure, temperature, hydrogen partial pressure and optionally inert gas partial pressure) over a predominantly heterogeneous catalyst. This mode of operation is described, for example, in the publications U.S. Pat. Nos. 4,314,084, 5,530,127, 5,932,769, FR 1347648, U.S. Pat. Nos. 3,270,059, 4,111,840, 4,123,462, DE 1667193, Fischer et al. (J. Catal., 1999, 182, 289-291) or Jenzer et al. (Catal. Lett., 1999, 61, 111-114).

A disadvantage of most heterogeneously catalyzed gas-phase processes is the use of high temperatures (up to 400° C.) and pressure (up to 300 bar), as a consequence of which frequently considerable amounts of higher amines, alkenes and alkanes are formed in addition to the desired primary amines. In addition, owing to the characteristic pressure and temperature conditions of a gas-phase reaction, only substrates which can be vaporized and reacted without losses or in the case of which the amines can be condensed or resublimed without losses can be converted in economical yields into amines by means of the abovementioned processes. Substrates or their corresponding amines, which are subject to decomposition under such conditions, are therefore reacted in liquid-phase syntheses in the literature and industry.

REDUCTIVE AMINATION

Processes known to those skilled in the art for preparing primary amines from alcohols by means of reductive amination utilize a multistage procedure which can be associated with a change in the oxidation state of the carbon atom bearing the hydroxyl groups. Processes which are carried out with retention of the oxidation state (direct amination) can be distinguished therefrom. With a change in the oxidation state of the carbon atom bearing the hydroxyl group (reductive amination), amines can classically be prepared by oxidation to the corresponding carbonyl compound, subsequent formation of the imine by reaction with an amine component (primary, secondary amine or ammonia) and subsequent homogeneously or heterogeneously catalyzed reduction of the imine by means of hydrogen. However, the two-stage mode of operation with isolation of the carbonyl compound is time-consuming and costly.

SPECIAL MULTISTAGE PROCESSES

With retention of the oxidation state of the carbon atom bearing the hydroxyl group (direct amination) alcohols can be converted by means of multistage substitution reactions into amines. Apart from the outlay for isolation of the intermediates, handling of, in particular, the explosive and toxic azides which are frequently employed here is disadvantageous in such processes. An exception to the multistage mode of operation for the direct amination of alcohols with retention of the oxidation state of the carbon atom bearing the hydroxyl group is, for example, the sequential reaction of primary alcohols with dialkyl azodicarboxylates, bis-tert-butyl iminodicarbonate and immobilized triphenylphosphane, which according to Sun et al. (Tetrahedron Lett., 2007, 48, 7745-7746), allows, after addition of trifluoroacetic acid, direct access to the primary amine without prior isolation of intermediates. Fabiano et al. (Synlett, 1987, 1987, 190-192) use the toxic hydrazoic acids instead of bis-tert-butyl iminodicarbonate for the same purpose.

DIRECT LIQUID-PHASE AMINATION OF ALCOHOLS

The direct single-stage liquid-phase amination of optionally polyhydric primary alcohols by means of ammonia has been described for some time in the scientific and patent literature. In some cases, the processes described cannot be classified unambiguously as gas- or liquid-phase processes because of the process conditions employed.

According to DE 19507007, ethanolamine can be aminated over oxide-supported ruthenium catalysts at temperatures of about 170° C. and a pressure of 200 bar to form ethylenediamine, with the achievable yields remaining below 40%.

The preparation of monovalent, optionally functionalized primary amines in high yields from the corresponding monohydric, optionally functionalized primary alcohols is described in the studies of Milstein et al. (Angew. Chem. Int. Ed., 2008, 47, 8661-8664). Here, the direct single-stage amination of sometimes heteroatom-substituted primary aliphatic and benzylic alcohols by reaction with excess ammonia in a solvent at 7.5 bar and a reaction temperature of 135-180° C. for from 12 to 36 hours is described. The air-stable acridinyl-based pincer complex carbonylchlorohydrido[4,5-(di-i-propylphosphinomethylacridino) ruthenium (II)] is used as catalyst, and yields in the range from 78 to 96% are achieved.

In addition, WO 2010018570 describes the use of quinolinyl-based pincer ligands with comparable yields.

A disadvantage of both published processes is that exclusively primary alcohols can be converted into amines thereby; this also corresponds to expectations, since it has frequently been stated that catalysts suitable for primary alcohols are not suitable for secondary alcohols. For example, Beller, M. et al., ChemSusChem, 2009, 2, 551-557, state that the catalyst mentioned there selectively converts the more reactive OH groups of a diol (primary OH group before secondary OH group; frequently secondary OH group before sterically hindered secondary OH group). Furthermore, Baiker et al. (J. Mol. Catal. A: Chem., 1999, 149, 197-204), show that the amination behaviour of primary diols is sensitive to the substitution pattern of the other carbon atoms present in the substrate, which again makes it obvious that the completely different environment of a secondary alcohol compared to a primary alcohol makes the use of a catalyst which works for primary alcohols unpromising.

A decrease in the selectivity of the formation of primary amines with increasing chain length of the alcohol substrate is known in the literature for functionalized secondary alcohols. Thus, Imm et al. (S. Imm, S. Bähn, L. Neubert, H. Neumann, M. Beller, Angew. Chem. 2010, 122 (44), 8303-6) describe a considerable decrease in the selectivity to the primary amine from 76 to 58%, when 4-phenyl-2-butanol instead of 3-phenyl-2-propanol is aminated in the presence of homogeneous Ru catalysts. In an analogous way, a significantly lower amine yield (51.2%) can be observed for 2-nonanol in the amination of aliphatic secondary alcohols than in the case of the lower homologue 2-octanol (67.1%) (D. Pingen, C. Müller, D. Vogt, Angew. Chem. 2010, 122 (44), 8307-10). It can therefore be assumed that higher and optionally additionally functionalized alcohols cannot be converted in high yields into the corresponding amines in this way.

The direct single-stage liquid-phase amination of functional, polyhydric alcohols by means of ammonia has been described exclusively over heterogeneous catalysts. The ether diol diethylene glycol was aminated in DE 3903367 by means of liquid ammonia over various zirconium dioxide-supported Cu—Co—Ni-catalysts at 200° C. in a 30 bar hydrogen atmosphere.

However, in no case was the ether diamine isolated as reaction product; merely aminoethoxyethanol and morpholine were obtained.

According to DE 1570542, polyether diols such as polypropylene glycol can be directly converted in high yields of up to 95.8% into the corresponding diamines when the reaction is carried out at 240° C. in the presence of Raney nickel catalysts. However, this mode of operation is also unsuitable for the conversion of thermolabile substrates, for example substrates derived from carbohydrates.

According to U.S. Pat. No. 4,153,581, polyether amines can be successfully prepared using a Co—Cu—Zn catalyst even at 140° C., but the catalyst is not suitable for secondary alcohols.

In related heterogeneously catalyzed processes, catalysts based on Co—Cr—Mn in the presence of $P_2O_5$ at 140-230° C. and 200-300 bar hydrogen pressure (DE 1543377), based on $Ni/Al_2O_3$ at 200-230° C. and 15-20 bar hydrogen pressure (RO 63243) or based on calcium silicoaluminates at 260-300° C. and 200 bar hydrogen pressure (DE 1278432) are also described.

Under comparable conditions, alcohols are aminated by the processes described in DE 19859776 (180-230° C. over Cu—$CuO/TiO_2$), DE 102006061045 (180-250° C. over Ni—$Cu/ZrO_2$), DE 102006061042 (180-220° C. over Ni—Cu—$Ru/ZrO_2$), WO 2008072428 (180-250° C. over $Ru/ZrO_2$) and WO2007077903 (180-250° C. over $Ru/Al_2O_3$); however, a hydrogen atmosphere is additionally required here.

The abovementioned examples indicate by way of example the need for processes which achieve activation of the alcohol even without the stoichiometric use of difficult-to-obtain and toxic auxiliaries. In addition, a critical disadvantage of all processes used hitherto for direct liquid-phase amination is that time-consuming and costly additional working steps have to be carried out for the formation and the optionally required isolation and purification of the intermediates occurring in the synthetic sequence.

Amino derivatives of anhydrohexitols such as isosorbide, isomannide or isoidide in particular, have hitherto been described in the literature as only obtainable by means of complicated processes. Thus, WO2008/145921 describes the formation of bisaminoalkyl derivatives of isosorbide which are obtained from the latter by addition onto acrylonitrile and subsequent hydrogenation.

Apart from the high temperatures frequently necessary in the above-described processes, a further disadvantage of the processes mentioned is that they have to be carried out in the presence of high hydrogen partial pressures in order to be able to obtain the target products in the desired yields.

The indicated prior art does not disclose any process which allows the direct, single-stage, hydrogen-free liquid-phase amination of optionally polyhydric secondary and optionally functionalized alcohols by means of ammonia to form primary amines in high yields under mild reaction conditions.

It was therefore an object of the present invention to provide a process for preparing primary amines from secondary alcohols, which avoids at least one of the abovementioned disadvantages and can be carried out economically advantageously.

DESCRIPTION OF THE INVENTION

We have now surprisingly found a process which allows the direct amination of secondary alcohols by means of ammonia in high yields in the presence of a catalyst as described in claim 1, with the secondary hydroxyl group of the alcohol being aminated.

The present invention therefore provides a process which allows the direct, homogeneously catalyzed liquid-phase amination of optionally polyhydric and/or functionalized, secondary alcohols using a superstoichiometric amount of ammonia based on hydroxyl groups to be aminated, preferably in the absence of hydrogen, where the process conditions employed allow in particular also the reaction of thermolabile alcohols, for example alcohols obtained from renewable raw materials.

An advantage of the process of the invention is that the isolation and purification of intermediates which is otherwise necessary in the reaction is avoided.

Another advantage is that the use of problematical auxiliaries such as azides can be avoided. A further advantage is that the formation of coproducts is avoided by the process of the invention. It is also advantageous that the alcohol is reacted in the dissolved state.

Another advantage is that the amination of the alcohol can be effected without isolation and/or purification of intermediates.

The process of the invention for preparing primary amines comprises the steps
A) provision of a solution of a secondary alcohol in a fluid, nongaseous phase,
B) contacting of the phase with free ammonia and/or at least one ammonia-releasing compound and a homogeneous catalyst and optionally
C) isolation of the primary amine formed in process step B), and is characterized in that the volume ratio of the volume of the liquid phase to the volume of the gas phase ($V_{liq}N_{gas}$) in process step B) is greater than or equal to 0.25, preferably greater than 0.3, in particular greater than 2, and/or the ammonia is used in process step B) in a molar ratio based on the hydroxyl groups in the secondary alcohol of at least 5:1, preferably 50:1, particularly preferably 500:1.

In the context of the present invention the term "primary amine" likewise refers to salts thereof and also mixtures of the amine and/or its salts.

In the context of the present invention the term "secondary alcohol" refers to an organic compound which has at least one secondary hydroxy group (R-CH(OH)-R' where R and R' are not H).

To calculate the volume ratio, the "gas phase" is considered to be the internal volume of the apparatus surrounding the reaction minus the volume of the liquid phase.

Possible homogeneous catalysts to be used in the process of the invention are all homogeneous catalysts known to those skilled in the art which are able to activate the CH bond of the carbon atom bearing the OH group to be aminated. Examples of such catalysts encompass alkali metal alkoxides, aluminium alkoxides and lanthanide alkoxides, inorganic compounds of noble metals (e.g. [RuCl$_3$*nH$_2$O], IrCl$_3$), monometallic or multimetallic, mononuclear or multinuclear coordination compounds of one or more noble metals selected from among the elements ruthenium (e.g. [RuCl$_2$(PPh$_3$)$_3$], [RuH$_2$(PPh$_3$)$_4$], the Shvo catalyst ([η$^4$-C$_4$Ph$_4$CO)Ru(CO)$_3$]$_2$), [Ru(cod)(cot)], [(PPh$_3$)$_2$Ru(CH$_3$CN)$_3$Cl]BPh$_4$, [Ru(p-cymene)Cl$_2$]$_2$, [Ru(p-cymene)Cl$_2$]$_2$/DPEphos, [Ru(PPh$_3$)$_3$(CO)H$_2$], [Ru$_3$(CO)$_{12}$], [Ru$_3$(CO)$_{12}$]/N-phenyl-2-(PCl$_2$)pyrrole, [RuCl$_2$(dmso)$_4$]), rhodium (e.g. the Wilkinson catalyst ([RhCl(PPh$_3$)$_3$]), [RhH(PPh$_3$)$_3$]), iridium (e.g. [IrCl$_3$(dmso)$_3$], [Cp*IrCl$_2$]$_2$, [Ir(cod)Cl]$_2$/(dppp)Cs$_2$CO$_3$, [IrCl$_2$H(cod)]$_2$, KOH-activated phenanthroline-iridium complexes) and palladium ([Pd(PPh$_3$)$_4$], [PdCl$_2$(dppe)], [Pd(OAc)$_2$]) and also of the other platinum metals and iron.

In a further preferred embodiment of the process of the invention, catalysts which are known to those skilled in the art as catalysts for hydroformylation are used in step B). For this purpose, it is possible to use transition metal-carbonyl compounds of the general formula H$_x$M$_y$M'$_{y'}$(CO)$_z$L$_n$, where n=0 ("unmodified hydroformylation catalysts") or n≠0 ("modified hydroformylation catalysts") and x, y and z are integers. y' can be zero when a monometallic catalyst is used, or y' can be a positive integer when a bimetallic catalyst is used. M and M' can be identical or different. As transition metals M and M', it is possible to use rhodium, cobalt, iridium, ruthenium, osmium, platinum, palladium, iron, nickel, chromium, molybdenum or manganese; preference is given to using rhodium, cobalt, iridium, ruthenium, osmium or platinum. The ligand L can be selected from the group consisting of phosphanes, phosphane oxides, phosphites, amines, amides, isonitriles, arsanes or stibanes; examples are triphenylphosphane, triphenylphosphane oxide, triphenylphosphanetrisulphonic acid sodium salt, triphenylamine or triphenylarsane.

Examples of hydroformylation catalysts are selected from the group consisting of HCo(CO)$_4$, HCo(CO)$_3$PBu$_3$, HRh(CO)(PR$_3$)$_3$, Rh$_4$(CO)$_{12}$, Rh$_6$(CO)$_{16}$, Rh$_2$(CO)$_4$Cl$_2$, CoRh(CO)$_7$, Co$_2$Rh$_2$(CO)$_{12}$, HRh(CO)$_3$.

A hydroformylation catalyst which is preferred in this context is a catalyst system containing at least one xantphos ligand of the general formula 1 and a transition metal compound.

In the context of the present invention, the term "xantphos ligand" refers to a compound of the general formula 1, General formula 1

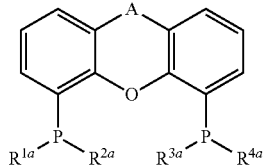

where
$R^{1a}$, $R^{2a}$, $R^{3a}$ and $R^{4a}$ are identical or different and are selected independently from the group containing, preferably consisting of, phenyl, tert-butyl and isopropyl, and
A is selected from the group containing, preferably consisting of, —C(CH$_3$)$_2$—, —CH$_2$CH$_2$—, —Si(CH$_3$)$_2$—, —S—, —O—, —C(C(CH$_3$)$_2$)—.

Preference is given to using xantphos ligands in which $R^{1a}$=$R^{2a}$=$R^{3a}$=$R^{4a}$=phenyl and A=—C(CH$_3$)$_2$—.

The transition metal is preferably selected from the group containing, preferably consisting of, ruthenium, cobalt, rhodium, iridium, nickel, palladium and platinum and also the other platinum metals and iron. The transition metal is particularly preferably selected from the group consisting of ruthenium, iridium and palladium; particularly preferably from the group consisting of ruthenium and iridium, in particular ruthenium.

It may be mentioned that, depending on the selected combination of the above-described elements forming the catalyst, this can have an electric charge and be used in the form of a salt formed with the aid of suitable counterions.

In a particularly preferred embodiment, the catalyst is the xanthene-based coordination compound carbonylchlorohydrido[9,9-dimethyl-4,5-bis(diphenylphosphino)xantheno]ruthenium(II):

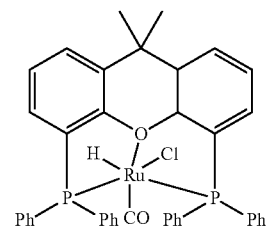

Carbonylchlorohydrido[9,9-dimethyl-4,5-bis(diphenylphosphino)xantheno]ruthenium(II)

In a further preferred embodiment of the process of the invention, pincer catalysts are used in step B).

As pincer catalysts used in process step B), it is possible to use coordination compounds of transition metals having the general structure A)

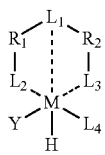

General structure A)

Here, in particular catalysts in which $L_1$ is a carbon atom or heteroatom, preferably nitrogen, serving as ligator for the central atom M, where M is a transition metal, to which further ligators $L_2$ and $L_3$ are covalently bound via the two divalent organic radicals $R_1$ and $R_2$, are advantageous for the process of the invention.

The central metal M is preferably selected from the group containing ruthenium, cobalt, rhodium, iridium, nickel, palladium and platinum. The central metal is particularly preferably selected from the group consisting of ruthenium, iridium and palladium; particularly preferably from the group consisting of ruthenium and iridium.

The divalent organic radicals $R_1$ and $R_2$ can, independently of one another, optionally contain further substituted aliphatic, alicyclic or aromatic structures which, together with the ligator $L_1$, optionally give a molecular unit whose configuration and conformation are fixed. The ligator $L_1$ is preferably part of a heterocyclic structure to which the radicals $R_1$ and $R_2$ are bound. $L_1$ is particularly preferably the nitrogen atom of an acridinyl or quinolinyl structure. This acridinyl or quinolinyl structure can bear one, two, three, four, five, six or seven substituents in any position, which together with the organic radicals $R_1$ and/or $R_2$ form a further aromatic unit fused onto the acridinyl or quinolinyl structure and can be selected from the group consisting of hydrogen, alkyl, cycloalkyl, aryl, heterocyclyl, heteroaryl, alkylcycloalkyl, alkylaryl, alkylheterocyclyl, alkylheteroaryl, halogen, nitro, ester, amide, cyano, alkoxy, alkylamino and arylamino radicals. In a preferred embodiment, $R_1$, $R_2$ and $L_1$ are constituents of a 4,5-dimethyleneacridine radical.

The ligators $L_2$ and $L_3$ covalently bound to the above-described unit formed by $R_1$, $R_2$ and $L_1$ are each further heteroatoms present in molecular radicals selected independently from the group comprising phosphine ($PR^aR^b$), amine ($NR^aR^b$), imine, sulphide ($SR^a$), thiol (SH), sulphoxide ($S(=O)R^a$), heteroaryl containing at least one atom selected from among nitrogen or sulphur, arsine ($AsR^aR^b$), stibine ($SbR^aR^b$) and N-heterocyclic carbene represented by the structures

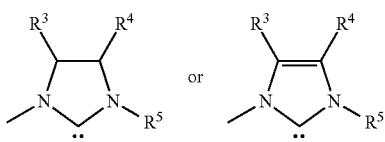

The ligator $L_4$ coordinated to the central metal described is a heteroatom present in a monodentate two-electron donor selected from the group CO, $PR^aR^bR^c$, $NO^+$, $AsR^aR^bR^c$, $SbR^aR^bR^{c*}$, $SR^aR^b$, nitrile ($R^aCN$), isonitrile ($R^aNC$), $N_2$, $PF_3$, CS, heteroaryl (e.g. pyridine, thiophene), tetrahydrothiophene or N-heterocyclic carbene.

Y is a monoanionic ligand selected from the group halogen, carboxylate, trifluoroacetate, sulphonate, trifluoromethanesulphonate, cyanide, hydroxide, alkoxide, imide; or else an uncharged solvate molecule such as $NH_3$, $NR^a$ $R^bR^c$, $R^aR^bNSO_2R^c$. Y is preferably selected from the group halide, acetone, dialkylacetone (e.g. 2-butanone), cyclic ketone (e.g. cyclohexanone), THF, anisole, DMSO, acetonitrile, dichloromethane, toluene, water, pyridine.

The radicals $R^3$, $R^4$, $R^5$, $R^a$, $R^b$ and $R^c$ are identical or different and are selected independently from the group alkyl, cycloalkyl, aryl, heterocyclyl, heteroaryl, alkylcycloalkyl, alkylaryl, alkylheterocyclyl and alkylheteroalkyl. The radicals $R^3$, $R^4$, $R^5$, $R^a$, $R^b$ and $R^c$ are preferably each selected independently from among methyl, ethyl, isopropyl, $^t$butyl, cyclohexyl, cyclopentyl, phenyl and mesityl.

It may be mentioned that, depending on the selected combination of the above-described elements forming the catalyst, this can have an electric charge and be used in the form of a salt formed with the aid of suitable counterions.

In a particularly preferred embodiment, the catalyst is the acridine-based coordination compound carbonylchlorohydrido[4,5-(di-i-propylphosphinomethylacridino)ruthenium (II)]:

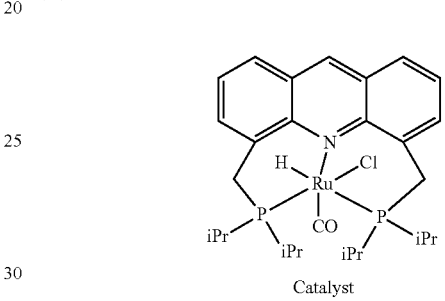

Catalyst

Carbonylchlorohydrido[4,5-(di-i-propylphosphinornethylacridino)ruthenium(II)]

The process of the invention can be utilized for the direct amination of secondary alcohols by means of ammonia to form primary amines. Alcohols which are preferably used in process step A) have at least two secondary hydroxy groups. These polyols are preferably characterized in that they can be vaporized only unsatisfactorily without decomposition, if at all, and are therefore not suitable for a gas-phase reaction; in particular these alcohols have a cyclic, preferably polycyclic, carbon skeleton. Such alcohols are, for example, carbohydrates, sugars, sugar alcohols or the derivatives which can be derived therefrom by means of chemical reactions (e.g. dehydrations), for example amino sugars, desoxy sugars, glycals, glycitols, and C- or O-glycosides.

Alcohols which are particularly preferably used in process step A) are selected from the group consisting of 2-dodecanol, cyclododecanol, 4-phenyl-2-butanol, isosorbide, isomannide, isoidite, polypropylene glycol, mannitol, sorbitol, galactitol and alkyl glycosides, with particular preference being given to using isomannide, 2-dodecanol, cyclododecanol and 4-phenyl-2-butanol. FIG. 1 shows the range of intermediates and products resulting from the process of the invention when starting out from the three isomers of 1,4:3,6-dianhydrohexitol, which represents secondary alcohols which are very particularly preferably used in the process of the invention.

The process of the invention can likewise be used advantageously for secondary alcohols which have a carboxy group or ester group, in particular a carboxy group.

Preferred secondary alcohols containing carboxy groups are, in particular, alpha-hydroxycarboxylic acids and OH-modified, natural fatty acids, where the OH-modified, natural fatty acids are selected, in particular, from the group derived from the fractions of coconut oil, kernel oils and castor oil.

Examples of such alcohols bearing a carboxy group are 2-hydroxypropionic acid (lactic acid), 2-hydroxy-3-methylbutanoic acid, 2-hydroxy-4-methylmercaptobutanoic acid, 2-hydroxy-4-methylpentanoic acid, 2-hydroxy-3-methylpentanoic acid, 2-hydroxy-3-(3-indyl)propionic acid, 2-hydroxy-3-phenylpropionic acid, 2-hydroxy-6-aminohexanoic acid, 2-hydroxy-5-guanidinopentanoic acid, 2-hydroxy-3-(1H-imidazol-4-yl)propanoic acid, 2-hydroxy-3-(4-hydroxyphenyl)propanoic acid, 2-hydroxy-4-aminocarbonylbutanoic acid, 2,3-dihydroxybutanoic acid, 2-hydroxypentanedioic acid, glycolic acid, 2,3-dihydroxypropanoic acid, 2-hydroxy-3-mercaptopropanoic acid, 2-hydroxy-3-aminocarbonylpropanoic acid and 2-hydroxysuccinic acid.

Preferred secondary alcohols containing ester groups are, in particular, selected from the group of alkyl esters, in particular the methyl esters, ethyl esters, n-propyl esters and isopropyl esters, of the hydroxycarboxylic acids.

In particular, the alcohols are selected from the group of the esters of OH-modified natural fatty acids and the esters of alpha-hydroxycarboxylic acids. Examples of this class of compounds are the methyl esters, ethyl esters, n-propyl esters and isopropyl esters of 2-hydroxypropionic acid (lactic acid), 2-hydroxy-3-methylbutanoic acid, 2-hydroxy-4-methylmercaptobutanoic acid, 2-hydroxy-4-methylpentanoic acid, 2-hydroxy-3-methylpentanoic acid, 2-hydroxy-3-(3-indyl) propionic acid, 2-hydroxy-3-phenylpropionic acid, 2-hydroxy-6-aminohexanoic acid, 2-hydroxy-5-guanidinopentanoic acid, 2-hydroxy-3-(1H-imidazol-4-yl)propanoic acid, 2-hydroxy-3-(4-hydroxyphenyl)propanoic acid, 2-hydroxy-4-aminocarbonylbutanoic acid, 2,3-dihydroxybutanoic acid, 2-hydroxypentanedioic acid, glycolic acid, 2,3-dihydroxpropanoic acid, 2-hydroxy-3-mercaptopropanioc acid, 2-hydroxy-3-aminocarbonylpropanoic acid and 2-hydroxysuccinic acid.

Illustrative alcohol concentrations used in the process of the invention are in the range from 0.1 to 10 000 mmol/l, preferably from 0.1 to 1000 mmol/l and particularly preferably from 1 to 100 mmol/l.

The fluid phase used in process step A) can be formed by a solvent or a gas which is present in liquefied or supercritical form under the process conditions, in particular ammonia, or mixtures of the components mentioned.

In this context, water or organic solvents or mixtures thereof can be used as solvent; these mixtures can be a homogeneous solution or else an emulsion. Particular preference is given to using at least one organic solvent. A nonlimiting selection of suitable organic solvents encompasses benzene, toluene, the xylene isomers, mesitylene, dioxane, THF, dimethoxyethane, anisole and cyclohexane.

In the context of the present invention, the ammonia or ammonia-releasing compounds used in process step B) also include, in particular, liquid or supercritical ammonia and/or a solution of ammonium salts in a solvent (e.g. ammonium hydroxide in water).

Gaseous or liquefied ammonia is preferably used as free ammonia in process step B).

In a preferred embodiment, process step B) is carried out under superatmospheric pressure. Illustrative pressures in the process of the invention are in the range from 1 to 1000 bar, preferably from 5 to 500 bar, particularly preferably from 5 to 100 bar and very particularly preferably from 20 to 50 bar. The pressure can be built up by injection of the ammonia and/or a further gas, in particular an inert gas such as nitrogen or argon, with the pressure preferably being built up by means of gas mixtures of the two.

The temperatures in process step B) of the process of the invention are in a range which keeps to a minimum the decomposition reactions of secondary alcohol, primary amine and all further intermediates occurring during the course of the process which, owing to thermal stress, lead to the formation of by-products. For example, the temperatures are in the range from 80 to 220° C., preferably from 100 to 200° C. and particularly preferably from 120 to 170° C., measured in the fluid phase.

According to the invention, the process is preferably carried out in the absence of hydrogen, where "absence of hydrogen" means that no hydrogen is additionally introduced into the reaction; any traces of hydrogen present in the air or the hydrogen formed from the substrate under the reaction conditions are not considered to be "in the absence of hydrogen" for the purposes of the present invention.

BRIEF DESCRIPTION OF THE FIGURES

FIG. 1: Scheme for the direct amination of dianhydrohexitols

EXAMPLES

Example 1

Direct Single-stage Amination of Isomannide by Means of Ammonia Over Heterogeneous Catalysts, Comparative Example 1.45 g of isomannide (10 mmol) and 2.78 g of a catalyst based on $Ni/Al_2O_3$ are placed in a high-pressure reactor provided with propeller stirrer and internal cooling coil and flushed with nitrogen at room temperature in the closed and gastight reactor. 250 ml of liquid ammonia (10 mol) are then metered in over a period of 25 minutes and the reaction mixture is heated in stages firstly to 150° C. (140 bar), then to 185° C. (260 bar). After a reaction time of 90 minutes, the reactor is cooled, vented, the reaction mixture is taken up in ethanol and filtered. No conversion of isomannide can be observed when using a catalyst based on elemental nickel.

Example 2

Direct Single-stage Amination of Isomannide by Means of Ammonia Over Coordination Compounds of Monodentate Ligands ($V_{liq}/V_{gas}$=0.35, Example According to the Invention)

Under an argon atmosphere, 1.461 g (10 mmol) of isomannide, 0.1 mmol of $[Ru(p-cym)Cl_2]_2/K_2CO_3$ and 25 ml of 2-methyl-2-butanol as solvent are placed in the glass liner of a 100 ml Hastelloy autoclave. The autoclave is closed, pressurized with 20 bar of argon and vented three times and again pressurized with 15 bar of argon. 235.2 mmol of ammonia are then introduced into the autoclave (overall $V_{liq}/V_{gas}$=0.35). The reaction mixture is stirred for 10 minutes at room temperature (600 rpm), subsequently heated while stirring to 140° C. and maintained at this temperature for 24 hours. After cooling to room temperature, careful depressurization of the mixture and pressurization with 20 bar of argon three times with subsequent venting, the autoclave is opened, the reaction mixture filtered through kieselguhr and the filtrate is evaporated under reduced pressure on a rotary evaporator to remove the solvent. The formation of the corresponding monoamino alcohol was confirmed.

Example 3

Direct Single-stage Amination of 2-dodecanol by Means of Ammonia Over a Ruthenium-pincer Complex ($V_{liq}/V_{gas}$=0.3, Accouding to the Invention)

Under an argon atmosphere, 1.863 g (10 mmol) of 2-dodecanol, 0.030 g (0.05 mmol) of carbonylchlorohydrido[4,5-(di-i-propylphosphinomethylacridino)ruthenium(II)] as catalyst and 25 ml of 2-methyl-2-butanol as solvent are placed in the glass liner of a 100 ml Hastelloy autoclave. The autoclave is closed, pressurized with 20 bar of argon and vented three times and again pressurized with 15 bar of argon. 2 g (117.6 mmol) of liquid ammonia are then introduced into the autoclave (overall $V_{liq}/V_{gas}$=0.3). The reaction mixture is stirred for 10 minutes at room temperature (600 rpm), subsequently heated while stirring to an internal temperature of 170° C. and maintained at this temperature for 48 hours. After cooling to room temperature, careful depressurization of the mixture and pressurization with 20 bar of argon three times with subsequent venting, the autoclave is opened, the reaction mixture filtered through kieselguhr and the filtrate is evaporated under reduced pressure on a rotary evaporator to remove the solvent. The crude product obtained is purified by bulb tube distillation under reduced pressure. This gives 1.241 g of 2-dodecylamine (yield: 67% of theory; boiling range: 170-180° C. air bath temperature at 11 mbar).

Example 4

Direct Single-dstage Amination of Cyclododecanol by Means of Ammonia Over a Ruthenium-pincer Complex ($V_{liq}/V_{gas}$=0.3, According to the Invention)

Under an argon atmosphere, 1.843 g (10 mmol) of cyclododecanol, 0.030 g (0.05 mmol) of carbonylchlorohydrido[4,5-(di-i-propylphosphinomethylacridino)ruthenium(II)] as catalyst and 25 ml of 2-methyl-2-butanol as solvent are placed in the glass liner of a 100 ml Hastelloy autoclave. The autoclave is closed, pressurized with 20 bar of argon and vented three times and again pressurized with 15 bar of argon. 2 g (117.6 mmol) of liquid ammonia are then introduced into the autoclave (overall $V_{liq}/V_{gas}$=0.3). The reaction mixture is stirred for 10 minutes at room temperature (600 rpm), subsequently heated while stirring to an internal temperature of 170° C. and maintained at this temperature for 48 hours. After cooling to room temperature, careful depressurization of the mixture and pressurization with 20 bar of argon three times with subsequent venting, the autoclave is opened, the reaction mixture filtered through kieselguhr and the filtrate is evaporated under reduced pressure on a rotary evaporator to remove the solvent. The crude product obtained is purified by bulb tube distillation under reduced pressure. This gives 1.427 g of cyclododecylamine (yield: 78% of theory; boiling range: 175-180° C. air bath temperature at 6 mbar).

Example 5

Direct Single-stage Amination of 4-phenyl-2-butanol by Means of Ammonia Over an Ru-pincer Complex ($V_{liq}/V_{gas}$=0.3, According to the Invention)

Under an argon atmosphere, 1.502 g (10 mmol) of 4-phenyl-2-butanol, 0.030 g (0.05 mmol) of carbonylchlorohydrido[4,5-(di-i-propylphosphinomethylacridino)ruthenium(II)] as catalyst and 25 ml of 2-methyl-2-butanol as solvent are placed in the glass liner of a 100 ml Hastelloy autoclave. The autoclave is closed, pressurized with 20 bar of argon and vented three times and again pressurized with 15 bar of argon. 2 g (117.6 mmol) of liquid ammonia are then introduced into the autoclave (overall $V_{liq}/V_{gas}$=0.3). The reaction mixture is stirred for 10 minutes at room temperature (600 rpm), subsequently heated while stirring to an internal temperature of 170° C. and maintained at this temperature for 48 hours. After cooling to room temperature, careful depressurization of the mixture and pressurization with 20 bar of argon three times with subsequent venting, the autoclave is opened, the reaction mixture filtered through kieselguhr and the filtrate is evaporated under reduced pressure on a rotary evaporator to remove the solvent. The crude product obtained is purified by bulb tube distillation under reduced pressure. This gives 0.945 g of 4-phenyl-2-butylamine (yield: 63% of theory, boiling range: 135-140° C. air bath temperature at 8 mbar).

Example 6

Direct Single-stage Amination of Isomannide by Means of Ammonia Over an Ru-pincer Complex, (According to the Invention, $V_{liq}/V_{gas}$=0.35)

Under an argon atmosphere, 1.461 g (10 mmol) of isomannide, 0.061 g (0.1 mmol) of carbonylchlorohydrido[4,5-(di-i-propylphosphinomethylacridino)ruthenium(II)] as catalyst and 25 ml of 2-methyl-2-butanol as solvent are placed in the glass liner of a 100 ml Hastelloy autoclave. The autoclave is closed, pressurized with 20 bar of argon and vented three times and again pressurized with 15 bar of argon. 4 g (235.2 mmol) of liquid ammonia are then introduced into the autoclave (overall $V_{liq}/V_{gas}$=0.35). The reaction mixture is stirred for 10 minutes at room temperature (600 rpm), subsequently heated while stirring to an internal temperature of 170° C. and maintained at this temperature for 48 hours. After cooling to room temperature, careful depressurization of the mixture and pressurization with 20 bar of argon three times with subsequent venting, the autoclave is opened, the reaction mixture filtered through kieselguhr and the filtrate is evaporated under reduced pressure on a rotary evaporator to remove the solvent. The crude product obtained is purified by bulb tube distillation under reduced pressure. This gives 1.290 g of a mixture of the diamines diaminoisomannide, diaminoisosorbide and diaminoisoidide in a ratio of 50:41:9 (yield: 90% of theory, boiling range 185-190° C. air bath temperature at 10 mbar).

Example 7

Direct Single-stage Amination of Tripropylene Glycol by Means of Ammonia Over a Homogeneous Ruthenium Catalyst (According to the Invention; $V_{liq}/V_{gas}$=0.3)

Under an argon atmosphere, 0.961 g (5 mmol) of tripropylene glycol, 0.0305 g (0.05 mmol) of carbonylchlorohydrido [4,5-(di-i-propylphosphinomethylacridino)ruthenium(II)] as catalyst and 25 ml of 2-methyl-2-butanol as solvent are placed in the glass liner of a 100 ml Hastelloy autoclave. The autoclave is closed, pressurized with 20 bar of argon and vented three times and again pressurized with 15 bar of argon. 2 g (2.95 ml; 117 mmol) of liquid ammonia are then introduced into the autoclave (overall $V_{liq}/V_{gas}$=0.3). The reaction mixture is stirred for 10 minutes at room temperature (600 rpm), subsequently heated while stirring to an internal temperature of 170° C. and maintained at this temperature for 48 hours, resulting in a pressure of 45 bar being established. After cooling to room temperature, careful depressurization of the mixture and pressurization with 20 bar of argon three times with subsequent venting, the autoclave is opened, the reaction mixture filtered through kieselguhr and the filtrate is evaporated under reduced pressure on a rotary evaporator to remove the solvent. The crude product obtained is purified by bulb tube distillation under reduced pressure. This gives the diamine of tripropylene glycol in a yield of 91% of theory, boiling range 90-95° C. air bath temperature at 10 mbar.

Example 8

Direct Single-stage Amination of Tripropylene Glycol Over a Homogeneous Ruthenium Catalyst (Not According to the Invention; $V_{liq}/V_{gas}=0.17$)

Under an argon atmosphere, 0.4805 g (2.5 mmol) of tripropylene glycol, 0.01525 g (0.025 mmol) of carbonylchlorohydrido[4,5-(di-i-propylphosphinomethylacridino)ruthenium (II)] as catalyst and 12.5 ml of 2-methyl-2-butanol as solvent are placed in the glass liner of a 100 ml Hastelloy autoclave. The autoclave is closed, pressurized with 20 bar of argon and vented three times and again pressurized with 15 bar of argon. 1 g (1.475 ml; 58.8 mmol) of liquid ammonia is then introduced into the autoclave (overall $V_{liq}/V_{gas}=0.17$). The reaction mixture is stirred for 10 minutes at room temperature (600 rpm), subsequently heated while stirring to an internal temperature of 170° C. and maintained at this temperature for 48 hours, resulting in a pressure of 45 bar being established. After cooling to room temperature, careful depressurization of the mixture and pressurization with 20 bar of argon three times with subsequent venting, the autoclave is opened, the reaction mixture filtered through kieselguhr and the filtrate is evaporated under reduced pressure on a rotary evaporator to remove the solvent. The crude product obtained is purified by bulb tube distillation under reduced pressure. The diamine of tripropylene glycol is obtained in a yield of 90% of theory.

Example 9

Direct Single-stage Amination of 2-octanol by Means of Ammonia Over a Homogeneous Ruthenium Catalyst (Variation of Pressure and $V_{liq}/V_{gas}$)

Under an argon atmosphere, $m_o$ g of 2-octanol, $m_{Ru}$ g of [carbonylchlorohydridotris(triphenyl-phosphane)ruthenium (II)] as catalyst, $m_P$ g of xantphos and $V_{LM}$ ml of 2-methyl-2-butanol as solvent are placed in the glass liner of a 314 ml Hastelloy autoclave. The autoclave is closed, pressurized with 5 bar of nitrogen, vented and cooled to −70° C. $m_A$ g of liquid ammonia are then condensed into the autoclave, the reactor is warmed again to room temperature and pressurized with p bar of nitrogen. The reaction mixture is stirred for 10 minutes at room temperature (600 rpm), subsequently heated while stirring to an internal temperature of 170° C. and maintained at this temperature for 48 hours. After cooling to room temperature, careful depressurization of the mixture and pressurization with 5 bar of nitrogen with subsequent depressurization, the autoclave is opened and the reaction mixture is analyzed by means of a gas chromatograph. Reaction parameters and also conversions and selectivities to the desired primary amine 2-octylamine are reported in Tab. 1. The results show that the selectivity to the target product can be increased both by increasing the $V_{liq}/V_{gas}$ ratio and also by increasing the pressure and by simultaneously increasing both parameters.

TABLE 1

| No. | $m_O$ [g][1] | $m_{Ru}$ [g][2] | $m_P$ [g][3] | $V_S$ [ml][4] | $m_A$ [g][5] | p [bar][6] | $V_{liq}/V_{gas}$ [—][7] | C [%][8] | S [%][9] |
|---|---|---|---|---|---|---|---|---|---|
| 8.1 | 3.2 | 0.7 | 0.42 | 24.6 | 9.8 | 0 | 0.14 | 100 | 74.6 |
| 8.2 | 3.2 | 0.7 | 0.42 | 24.6 | 9.8 | 40 | 0.14 | 100 | 92 |
| 8.3 | 16.3 | 3.57 | 2.18 | 125.2 | 37.5 | 0 | 1.68 | 65 | 89 |
| 8.4 | 16.3 | 3.57 | 2.18 | 125.2 | 37.5 | 40 | 1.68 | 75 | 83.7 |

[1] mass of 2-octanol;
[2] mass of [carbonylchlorohydridotris(triphenylphosphane)ruthenium(II)];
[3] mass of xantphos;
[4] volume of solvent;
[5] mass of ammonia;
[6] nitrogen pressure set before reaction;
[7] ratio of the liquid phase volume to the gas phase volume;
[8] conversion of 2-octanol;
[9] selectivity to 2-octylamine.

The invention claimed is:

1. A process for preparing a primary amine, the process comprising:
   i) preparing a solution of a secondary alcohol and a homogeneous catalyst in a fluid, nongaseous phase;
   ii) contacting the solution with free ammonia, at least one ammonia-releasing compound, or both, in an amount such that a molar ratio of the ammonia to hydroxyl groups in the secondary alcohol is at least 5:1;
   iii) reacting the ammonia with the secondary alcohol under a pressure of 5 to 500 bar to maintain a two phase reaction comprising a liquid phase and a gas phase to obtain the primary amine; and
   iv) optionally isolating the primary amine obtained;
   wherein:
   a volume ratio of the liquid phase to the gas phase in the reaction is greater than or equal to 0.25.

2. The process according to claim 1, wherein the homogeneous catalyst is
   an alkali metal alkoxide, an aluminium alkoxide, a lanthanide alkoxide, an inorganic compound of noble metals,
   a monometallic or multimetallic, mononuclear or multinuclear coordination compound of at least one noble metal selected from the group consisting of ruthenium, iridium, rhodium, osmium, palladium, platinum and iron,
   or any mixture thereof.

3. The process according to claim 1,
   wherein
   the secondary alcohol comprises at least two secondary hydroxy groups.

4. The process according to claim 1,
   wherein
   the secondary alcohol comprises a cyclic or polycyclic carbon skeleton.

5. The process according to claim 1,
   wherein
   the secondary alcohol is selected from the group consisting of:
   2-dodecanol, cyclododecanol, 4-phenyl-2-butanol, isosorbide, isomannide, isoidite, polypropylene glycol, mannitol, sorbitol, galactitol and an alkyl glycoside.

6. The process according to claim 1,
wherein
the secondary alcohol is selected from the group consisting of an alpha-hydroxycarboxylic acid and an OH-modified, natural fatty acid.

7. The process according to claim 1,
wherein a liquid or supercritical ammonia, a solution of ammonium salts in a solvent, or both is used in said contacting ii).

8. The process according to claim 1,
wherein
said contacting ii) is carried out under a superatmospheric pressure.

9. The process according to claim 1,
wherein
said contacting ii) is carried out at a temperature of from 80 to 220° C.

10. The process according to claim 1,
wherein the homogeneous catalyst comprises
a hydroformylation catalyst comprising a xantphos ligand of a general formula 1 and a transition metal compound

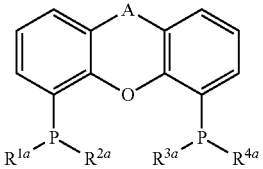

general formula 1 wherein $R^{1a}$, $R^{2a}$, $R^{3a}$, and $R^{4a}$ are each selected independently from the group consisting of phenyl, tert-butyl, and isopropyl, and
A is selected from the group consisting of —C(CH$_3$)$_2$—, —CH$_2$CH$_2$—, —Si(CH$_3$)$_2$—, —S—, —O—, and —C(C(CH$_3$)$_2$)—.

11. The process according to claim 1,
wherein the homogeneous catalyst comprises a pincer catalyst.

12. The process according to claim 11,
wherein the homogeneous catalyst comprises
a coordination compound of transition metals of a general structure A)

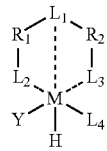

general structure A)

wherein
M is a transition metal,
L$_1$ is a heteroatom as a ligator for M,
L$_2$ and L$_3$ are each heteroatoms in molecular radicals and are each selected independently from the group consisting of a phosphine PR$^a$R$^b$, an amine NR$^a$R$^b$, an imine, a sulphide SR$^a$, a thiol SH, a sulphoxide S(=O) R$^a$, a heteroaryl comprising an atom selected from the group consisting of nitrogen and sulphur, an arsine AsR$^a$R$^b$, a stibine SbR$^a$R$^b$ and an N-heterocyclic carbene represented by

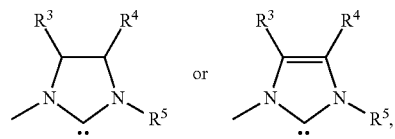

wherein L$_4$ is a heteroatom in a monodentate two-electron donor selected from the group consisting of a CO, a PR$^a$R$^b$R$^c$, an NO$^+$, an AsR$^a$R$^b$R$^c$, a SbR$^a$R$^b$R$^{c*}$, a SR$^a$R$^b$, a nitrile (R$^a$CN), an isonitrile (R$^a$NC), N$_2$, PF$_3$, CS, a heteroaryl, a tetrahydrothiophene and an N-heterocyclic carbene,
Y is a monoanionic ligand selected from the group consisting of a halogen, a carboxylate, a trifluoroacetate, a sulphonate, a trifluoromethanesulphonate, a cyanide, a hydroxide, an alkoxide, an imide, and an uncharged solvate molecule,
R$_1$ and R$_2$ are each independently a divalent organic radical, and
R$^3$, R$^4$, R$^5$, R$^a$, R$^b$ and R$^c$ are each selected independently from the group consisting of an alkyl, a cycloalkyl, an aryl, a heterocyclyl, a heteroaryl, an alkylcycloalkyl, an alkylaryl, an alkylheterocyclyl and an alkylheteroalkyl.

13. The process according to claim 11,
wherein the homogeneous catalyst comprises
carbonylchlorohydrido [4,5-(di-i-propylphosphinomethylacridino)ruthenium(II)].

* * * * *